United States Patent
Coppens et al.

(10) Patent No.: US 7,063,461 B2
(45) Date of Patent: Jun. 20, 2006

(54) PATIENT SUPPORT DEVICE WITH SHOULDER DEPRESSION DEVICE

(75) Inventors: Daniel D. Coppens, Avondale, PA (US); John A. Crowell, Wilmington, DE (US); David L. Simmons, Ocean, NJ (US); Gary Gearon, Shohola, PA (US); John Damon Kirk, Ramsey, NJ (US); David M. Rabeno, Bear, DE (US); Thomas R. Winward, New Castle, DE (US)

(73) Assignee: QFIX Systems, LLC, Avondale, PA (US)

( * ) Notice: Subject to any disclaimer, the term of this patent is extended or adjusted under 35 U.S.C. 154(b) by 0 days.

(21) Appl. No.: 10/452,680

(22) Filed: May 30, 2003

(65) Prior Publication Data

US 2004/0123388 A1 Jul. 1, 2004

Related U.S. Application Data

(60) Provisional application No. 60/428,029, filed on Nov. 21, 2002, provisional application No. 60/465,572, filed on Apr. 25, 2003.

(51) Int. Cl.
*A61B 6/04* (2006.01)
*A61G 13/12* (2006.01)

(52) U.S. Cl. .............................. 378/208; 5/637; 5/622

(58) Field of Classification Search .................... 5/601, 5/628, 621–625, 657, 652, 637; 378/208, 378/209; 600/415; 128/869
See application file for complete search history.

(56) References Cited

U.S. PATENT DOCUMENTS

| | | | |
|---|---|---|---|
| 2,787,262 A * | 4/1957 | Warner | 606/243 |
| 3,152,802 A * | 10/1964 | Heisler et al. | 5/621 |
| 4,256,112 A | 3/1981 | Kopf et al. | |
| 4,504,050 A | 3/1985 | Osborne | |
| 4,592,352 A * | 6/1986 | Patil | 606/130 |
| 4,669,106 A * | 5/1987 | Ammerman | 378/208 |
| 4,979,519 A | 12/1990 | Chavarria et al. | |
| 5,207,716 A | 5/1993 | McReynolds et al. | |
| 5,265,625 A * | 11/1993 | Bodman | 5/637 |
| 5,343,580 A * | 9/1994 | Bonutti | 600/415 |
| 5,349,956 A | 9/1994 | Bonutti | |
| 5,775,337 A | 7/1998 | Hauger et al. | |
| 5,806,116 A | 9/1998 | Oliver et al. | |
| 5,832,550 A | 11/1998 | Hauger et al. | |
| 5,848,449 A | 12/1998 | Hauger et al. | |
| 5,991,651 A * | 11/1999 | LaBarbera | 600/415 |
| 6,161,237 A | 12/2000 | Tang et al. | |
| 6,223,749 B1 * | 5/2001 | Beaty | 128/869 |
| 6,371,119 B1 * | 4/2002 | Zadini et al. | 128/845 |
| D462,448 S | 9/2002 | Huttner | |
| 6,442,777 B1 | 9/2002 | Pauli | |
| 6,484,332 B1 | 11/2002 | Korver, II et al. | |
| 6,622,324 B1 * | 9/2003 | VanSteenburg et al. | 5/621 |
| 6,698,045 B1 * | 3/2004 | Coppens et al. | 5/637 |
| 2003/0159216 A1 * | 8/2003 | Tomcany et al. | 5/628 |
| 2004/0133980 A1 | 7/2004 | Coppens | |

* cited by examiner

*Primary Examiner*—Michael Safavi
(74) *Attorney, Agent, or Firm*—Gomez International Patent Office, LLC; Brian A. Gomez

(57) ABSTRACT

A patient support device with shoulder depression devices for accurately and repeatably positioning a patient on a treatment table. The patient support device includes a headrest frame and an adjustable shoulder depression device and optionally includes a torso positioning device and a buttock restraint device.

32 Claims, 6 Drawing Sheets

PATIENT SUPPORT DEVICE WITH SHOULDER DEPRESSION DEVICE

CROSS-REFERENCE TO RELATED APPLICATIONS

This application claims the benefit of U.S. Provisional Application No. 60/428,029, filed Nov. 21, 2002 and U.S. Provisional Application No. 60/465,572, filed Apr. 25, 2003.

BACKGROUND OF THE INVENTION

The present invention relates to a durable and adjustable patient support device with shoulder depression device for repeatably positioning a patient for treatment. The patient support device of the present invention has several applications where immobility of the head and neck is required and an unobstructed 360-degree treatment is desired. The present invention is uniquely adjustable and is capable of repeatably positioning a patient by immobilizing the patient's head, neck, shoulders and torso.

A major application of the present invention can be for patients in treatment settings who require radiation treatment of cancer within the brain and neck. When a high energy beam is used for irradiation of the tumor, it is critical that the beam destroys the tumor but not the surrounding healthy tissue. In order to accomplish this objective with acceptable precision, it is critical that the head and neck be maintained in a precise and fixed position with no possibility of movement.

Reproducible immobilization is essential to a tighter and more conformed treatment field. By precisely positioning and repositioning a patient, a high-energy beam can be repeatably applied to a tumor. This allows for a higher dose of radiation to the gross tumor volume without affecting healthy tissue.

There are immobilization devices on the market today with various deficiencies and shortcomings. Such deficiencies include incompatibility with available accessories or tables, an inability to cantilever out from a treatment table, as well as an inability to accurately and repeatably immobilize the head, neck, shoulders and torso. In addition, several patient positioning devices are not sufficiently radiolucent.

Radiolucency is highly desirable and can provide tremendous benefit to a patient. For example, several patient positioning devices contain metallic parts. In radiation therapy, metallic parts are not desirable, especially if they are in the treatment field. Metallic parts can cause increased elastic and inelastic radiation scattering as well as fluorescence which can expose the patient to unnecessary radiation. While the use of metals can cause unwanted radiation exposure, they can also reduce the desired radiation dose that reaches the target area due to their high radiation absorption compared to polymer and carbon fiber composites used in the present invention.

Some positioning devices are constructed of acrylic which provide a lower strength to attenuation ratio than those constructed of carbon fiber composites. In addition, some positioning devices do not cantilever out over a treatment table thereby allowing an unobstructed 360-degree treatment of the head and neck. Furthermore, there are no commercial devices available that include shoulder depression devices for restricting a patient's movement or torso positioning devices for immobilizing the torso. The only shoulder depression devices currently available include the use of fabric straps. The straps can be imprecisely adjusted to restrict the patient's movement. However, the straps are cumbersome to use, do not sufficiently immobilize the patient and cannot accurately and repeatably position the patient. Finally, there are no commercially available devices that cantilever off the treatment table and incorporate an angling head immobilization device.

The present invention overcomes these deficiencies provides a durable patient support device for immobilizing a patient and allows precise, efficient and repeatable adjustability in a light weight carbon fiber composite that is radiolucent.

SUMMARY OF THE INVENTION

The patient support device of the present invention provides a head, shoulder and torso support and immobilization device that is adaptable to most commercially available treatment tables, is easily adjustable and provides efficient repeatability while allowing 360-degree treatment of the head and neck. The head, shoulder and torso support and immobilization device of the present invention can be constructed entirely of non-metallic components and provides exceptional radiolucency. Specifically, the present invention provides a patient support device for accurately and repeatably positioning a patient on a treatment table, comprising a base frame adaptable to be secured to a treatment table; at least one adjustable shoulder depression device retentively secured to the base frame; and a headrest frame that is adaptable to receive a head restraint assembly. A preferred embodiment of the present invention optionally provides a torso positioning device for further restricting a patient's movement. Yet another embodiment includes a patient support device further comprising a buttock restraint means.

A further embodiment includes a patient support device wherein the headrest frame is a pivotable and angling head immobilization device comprising, a base frame adaptable to be secured to a treatment table; at least one indexing ladder retentively and detachably secured to the base frame; a pivotable headrest frame secured to the base frame that is adapted to receive a head restraint assembly; and a slide locking mechanism with at least one index tab for use with the indexing ladder.

A further embodiment includes a shoulder depression device for use with a patient support device comprising a notched slide arm that can be retentively received by the patient support device.

DETAILED DESCRIPTION OF THE INVENTION

Figure 1:
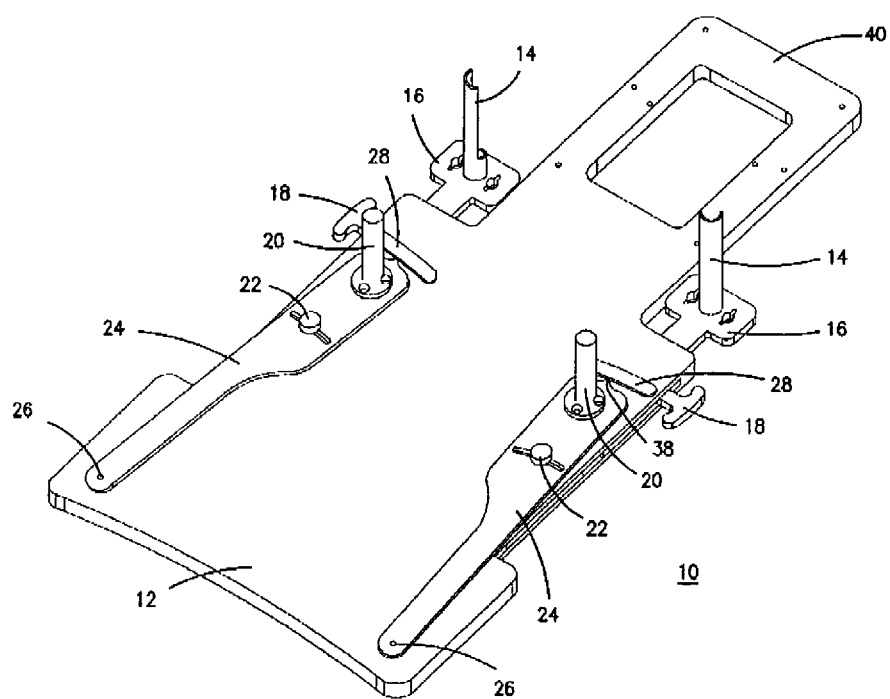
FIGS. 1 and 2 are illustrations of a typical assembly of the present invention.
Figure 2:
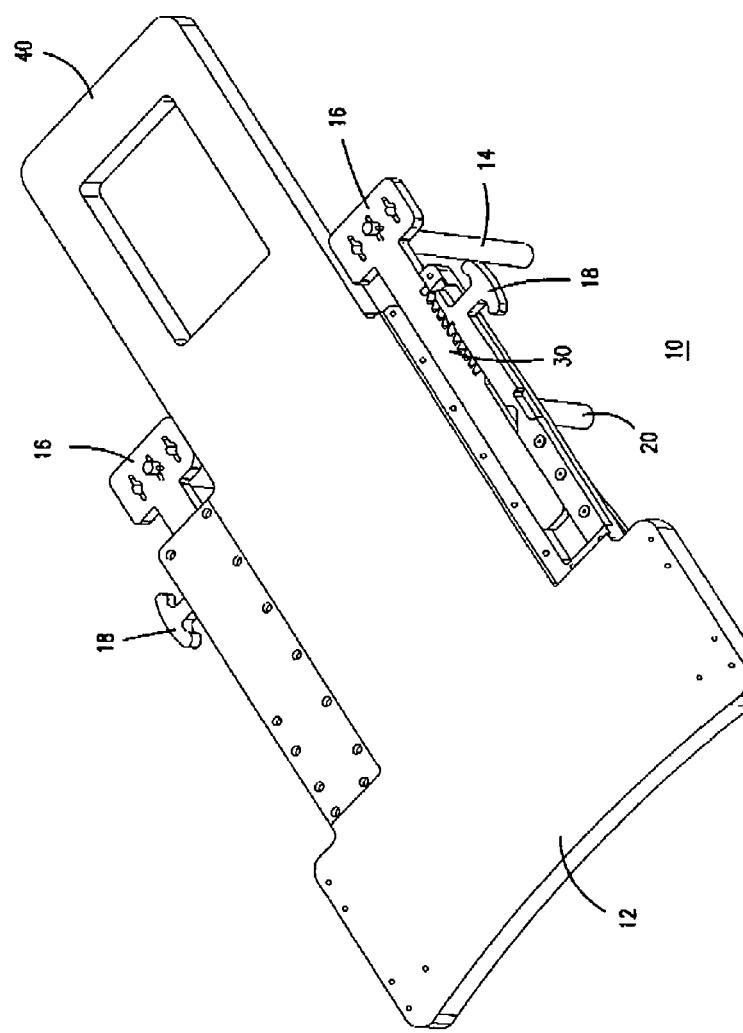

The present invention provides a radiolucent device that is easily adaptable to most treatment tables. Referring to the drawings, the patient support device of the present invention is designated by reference numeral 10. FIG. 1 shows the patient support device of the present invention for use with a patient in the supine position. The patient support device of the present invention consists of a base frame 12. FIGS. 1 and 2 depict a one-piece construction of the headrest frame 40 connected to the base frame 12 that is adaptable for receiving a head restraint assembly. Although not shown, the present invention also considers a two-part construction with the headrest frame attached to the base frame 12 by various attachment means. In addition, the present invention contemplates the integration of an angling head immobilization device to the base frame in order to further manipulate and repeatably position a patient. The head restraint assembly and the angling head immobilization device have been fully disclosed and described in an application Ser. No. 10/287,063, filed on Nov. 4, 2002, as Anholt-4 now issued as U.S. Pat. No. 6,698,045 to Coppens, et al. The present application hereby incorporates that application in its entirety.

Figure 4:
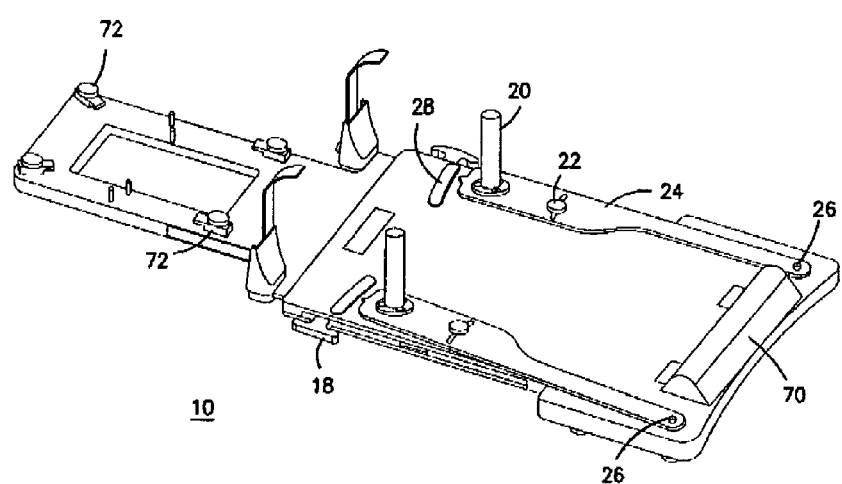
FIG. 4 is an illustration of a typical assembly of the present invention.

As depicted in FIG. 4, the present invention also contemplates the inclusion of a support device that prevents the pressure placed on the patient's shoulders from causing the patient to slide inferiorly down the board. This can be accomplished by the addition of a buttock restraint means 70. The buttock restraint means can be a simple raised pad attached to the base frame 12 or a more complex shaped or molded design that cradles the buttocks so that inferior movement is restricted. The buttock restraint means can be indexed for accurate and repeatable positioning.

Figure 3:
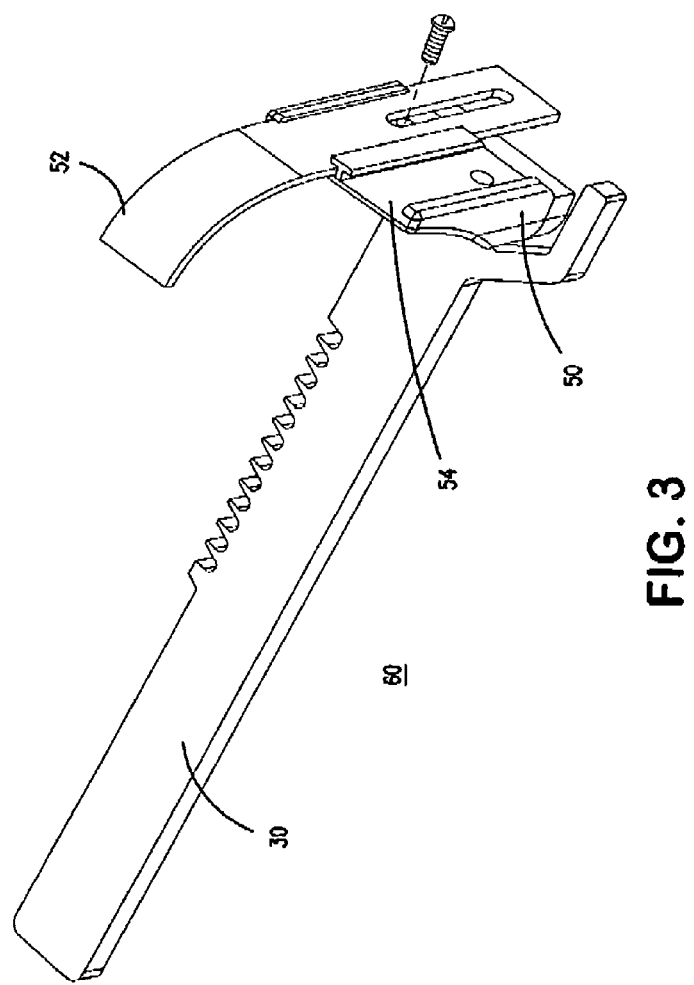
FIG. 3 is an illustration of one aspect of a shoulder depression device of the present invention.

FIGS. 1 and 2 show the depression post 14 as a vertical tube positioned at the one end of the shoulder depression device 16. The present invention contemplates various depression means including a shaped tube, post or bar that curves around a patient's shoulders and can extend to the upper torso. With this alternative embodiment, the patient's upper body movement is further restricted by pressing the shoulders to the surface of the cantilever board and toward the feet. The appropriate depression of the shoulders can be accomplished with various designs including a bear claw shape and other obvious design alternatives. FIG. 3 shows a preferred embodiment of the shoulder depression device 60 which is a bear claw design. The bear claw design includes the notched slide arm 30 with a shoulder post base 50 attached at one end. The shoulder post base 50 has at least one shoulder depression post 52 that slides into at least one shoulder post base slot 54. A preferred embodiment of the present invention includes a pivotable and indexed shoulder post base 50. The shoulder post base 50 can be equipped with at least one locking means selected from the group consisting of a screw, clamp, cam, clip, pin and spring. It will be clear to those skilled in the art that the present invention contemplates several different shapes and sizes of depression means without departing from the scope of the invention.

The shoulder depression device 16 comprises a notched slide arm 30 that is slidably and retentively received by the base frame 12. The notched slide arm 30 comprises notches that oppose at least one notch on the base frame 12 and a release mechanism 18 for disengaging the slide arm 30 from the base frame 12. The patient support device has an optional torso positioning device 24 that is pivotably secured to the base frame 12 at one end 26. At the opposite end, the torso positioning device 24 has at least one stabilizing post 20 for restrictively contacting a patient's torso. The torso positioning device 24 comprises a locking mechanism 22 that can lock the device in a precise and repeatable position. The device has a pointer 38 at the end opposite of the pivot end, which corresponds to an indexing gauge/strip 28 attached to the base frame 12. This way, the torso positioning device 24 can be adjusted thereby allowing repeatable positioning of a patient.

Figure 5:
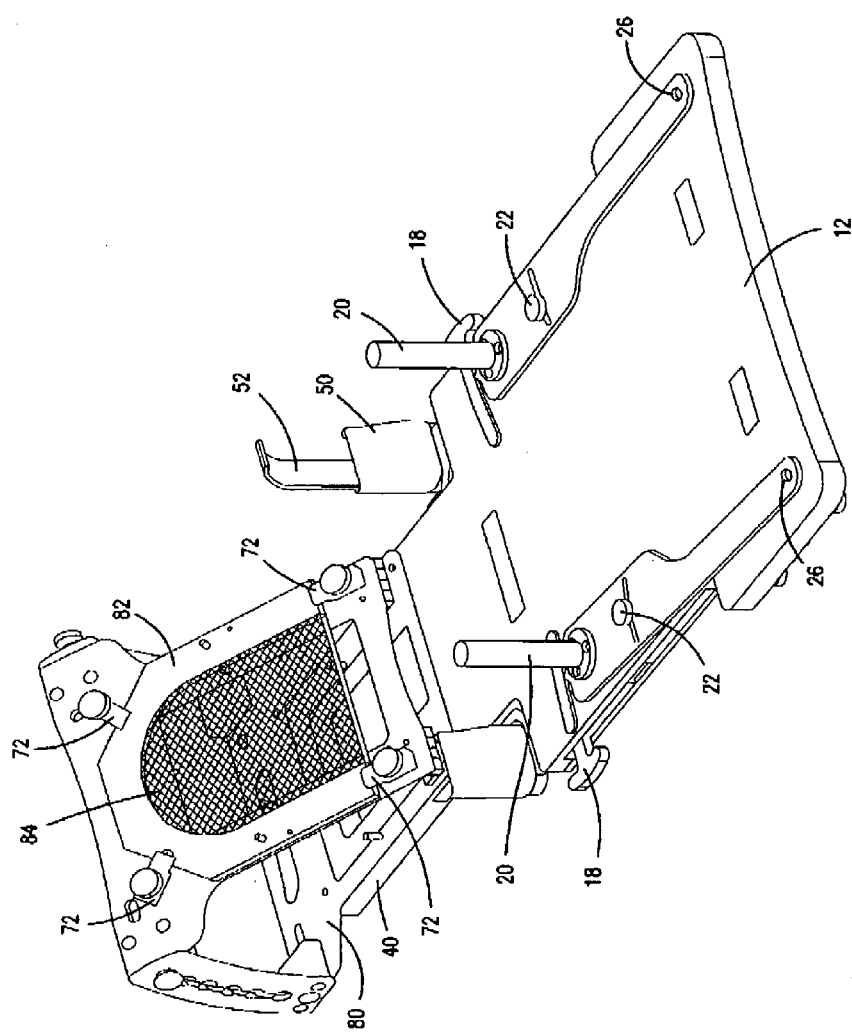
FIG. 5 shows a head restraint assembly attached to the base frame.
Figure 6:
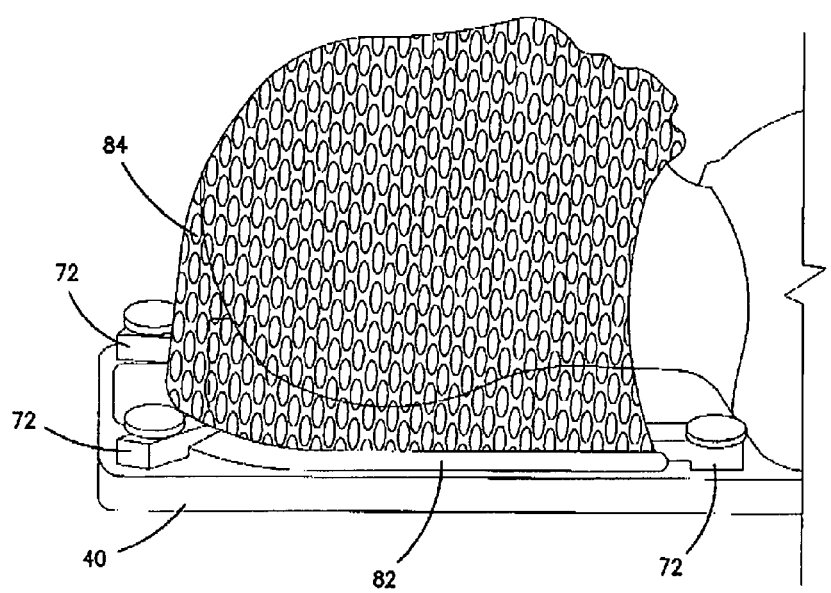
FIG. 6 illustrates a headrest frame with the thermoplastic mask stretched over and immobilizing a patient's head.

FIG. 5 shows a head restraint assembly 80 attached to the headrest frame 40. The head restraint assembly 80 includes an angling head immobilization device with a U-shaped insert 82 and a deformable thermoplastic mask 84 attached to the U-shaped insert. In this depiction, the head restraint assembly is attached to a one piece construction of the base frame 12 and headrest frame 40. FIG. 6 shows the U-shaped insert 82 attached by retaining clips 72 directly to the headrest frame 40. The thermoplastic mask 84 is stretched over and immobilizing the patient's head.

The patient support device of the present invention 10 can be attached to most standard patient tables or couches by various attachment means. The securing means can be a removable device or it can be integrated into the base frame 12 with appropriately placed holes and pins so that it universally fits most common patient tables.

It is understood that the dimensions may vary from that shown in the drawings and the drawings are presented for illustrative purposes only. The precise shapes and dimensions of the invention can be changed without departing from the object of the present invention. Furthermore, the arrangement and specific design may change without departing from the scope of the invention.

The patient support device of the present invention is adjustable in several ways. First, the device can be adjusted to fit most commercially available treatment tables. This adjustability provides complete flexibility in that the device of the present invention is self-contained and fits most existing procedure tables. There is no need for retrofitting or additional clamping or securing means. The patient support device of the present invention adjusts on two sides and can easily be centered on a procedure table because of its two-way adjustability.

The patient support device of the present invention also has head, neck, shoulder and torso adjustment means. In addition, the patient support device can have an angling head immobilization device integrated to the base frame 12. With this embodiment, the device has an angle positioning and locking mechanism that allows fixed, repeatable and incremental changes in the angle at which the head rests.

All components of the present invention can be non-metallic although some metallic parts can be used if they do not disrupt the performance of the device. Performance of the device is directly influenced by the material used for its construction. Lighter elements are preferred over heavier elements. For example, the lighter elements in composites and polymer materials result in less elastic and inelastic radiation scattering compared to materials containing metals or alloys. In addition, fluorescence is reduced. For example, when a metal atom is impacted by radiation, it absorbs the radiation energy by ejecting an electron from its shell in the atom's electron cloud. When an electron falls back into the shell, radiation is emitted. This effect is known as fluorescence. Because the radiation can be emitted in any direction, the patient can be subjected to an undirected dose of radiation energy. Metals are also undesirable due to their high radiation absorption compared to plastics and carbon composite. Because of the high radiation absorption, the use of metals in the device can also reduce the therapy dose available to the patient.

The individual components can be selected based on the intended use of the device but typically are crafted out of materials that provide exceptional radiolucency, such as carbon composite. This particular feature is especially important if a highly oblique angle must be used for treating the patient where the device could come into the line of the high-energy beam. A radiolucent device allows imaging and treatment of a patient through the patient support device. This increases the treatment flexibility by allowing an accurate attack of the cancer or tumor from all aspects and angles.

The present invention can be used in conjunction with most available tables as well as most available accessories that can be used with the patient support device. One such accessory is a readily available deformable low temperature thermoplastic mask. One such product is a specialty mask currently sold by WFR/Aquaplast which can be attached to the present invention. The thermoplastic mesh mask is formed to fit the patient's features and dimensions and is attached to the headrest frame 40 in order to restrict the patient's movement and accurately and repeatably position the patient for treatment. The attachment means can be one or more clips 72, as shown in FIG. 4, or any other means recognizable by one skilled in the art.

This description and the Figures illustrate one example of the present invention and are in no way meant to be limiting. Several different specific designs are contemplated by the inventors without parting from the original scope of the present invention and would be easily recognizable by those skilled in the art. Whereas the invention has been shown and described in connection with the preferred embodiments thereof, it will be understood that many modifications, substitutions and additions can be made which are within the intended broad scope of the following claims.

We claim:

1. A patient support device for accurately and repeatably positioning a patient on a treatment table, comprising:
   a base frame adaptable to be secured to a treatment table;
   at least one indexed and adjustable shoulder depression device retentively and detachably secured to the base frame; and
   a headrest frame that is adaptable to receive a head restraint assembly, wherein the shoulder depression device comprises a horizontal notched slide arm and wherein the notched slide arm moves substantially parallel to the patient and comprises at least one shoulder depression post or bar for contacting and depressing a patient's shoulders, and wherein the base frame slidably and retentively receives the horizontal notched slide arm and wherein the base frame has at least one notch opposing at least one notch on the notched slide arm for slidably and retentively receiving the notched slide arm.

2. A patient support device of claim 1, further comprising a buttock restraint means.

3. A patient support device of claim 1, wherein the shoulder depression device is integrated into the base frame and the notched slide arm is adjustable and indexed and can be repeatably ratcheted in to position in order to firmly immobilize the patient's shoulders.

4. A patient support device of claim 1, wherein the notched slide arm comprises a shoulder post base for slidably and retentively receiving the at least one shoulder depression post or bar for contacting and depressing a patient's shoulders.

5. A patient support device of claim 4, wherein the at least one shoulder post base comprises at least one slot to mateably receive the at least one shoulder depression post.

6. A patient support device of claim 4, wherein the at least one shoulder depression post is pivotable and indexed.

7. A patient support device of claim 4, wherein the at least one shoulder depression post is locked in place with a locking means.

8. A patient support device of claim 7, wherein the locking means is at least one selected from the group consisting of a screw, clamp, cam, clip, pin and spring.

9. A patient support device of claim 4, wherein the at least one shoulder depression post is shaped to fit over the patient's shoulders.

10. A patient support device of claim 1, wherein the shoulder depression device includes a release mechanism for disengaging the notched slide arm from the at least one opposing notch on the base frame.

11. A patient support device of claim 1, further comprising at least one torso positioning device movably attached to the base frame.

12. A patient support device of claim 11, wherein the at least one torso positioning device has a pivot end and an indexed end, and the indexed end has a stabilizing post for contacting and positioning a patient's torso.

13. A patient support device of claim 1, wherein the board is constructed of carbon composite.

14. A patient support device or claim 1, wherein the board is radiolucent.

15. A patient support device of claim 1, wherein the head restraint assembly comprises a U-shaped insert and a deformable mesh sheet attached thereto, that is capable of forming a mask over a patient's head.

16. A patient support device of claim 1, wherein at least one end of the base frame extends beyond at least one edge of the treatment table thereby allowing for unobstructed 360° treatment of a patient's head and neck region.

17. A patient support device of claim 1, wherein the headrest frame is a pivotable and angling head immobilization device comprising:
   a base frame adaptable to be secured to a treatment table;
   at least one indexing ladder retentively and detachably secured to the base frame; and
   a pivotable headrest frame secured to the base frame that is adapted to receive a head restraint assembly.

18. A patient support device of claim 17, wherein the at least one indexing ladder and the pivotable headrest frame can fold flat with the base frame.

19. A patient support device of claim 17, wherein the pivotable headrest frame has at least one guide pin for positioning the mask to the pivotable headrest frame.

20. A patient support device of claim 19, wherein the pivotable headrest frame has at least one securing clip for locking the head restraint assembly to the pivotable headrest frame.

21. A patient support device of claim 17, wherein the pivotable headrest frame has at least one removable guide post for receiving the head restraint assembly while forming the patient mask.

22. A patient support device of claim 17, wherein the base frame has at least one adjustable riser block, wherein the pivotable headrest frame has a pivot end and an indexing end and the pivot end is secured to the at least one riser block.

23. A patient support device of claim 22 wherein the pivotable headrest frame can be indexed between about −15 and 45 degrees with respect to horizontal.

24. A patient support device of claim 23 for accommodating a patient in a prone position.

25. A patient support device of claim 17 wherein the angling head immobilization device is radiolucent and allows imaging and treatment of a patient through the head immobilization device.

26. A patient support device of claim 17 adaptable for use in patient imaging and treatment including diagnostic imaging of the head and neck, whole brain tumor treatments, treatment of tumors in the neck region, cranio-spinal axis technique and pituitary gland treatment.

27. A patient support device of claim 17, wherein the device is made from carbon composite.

28. A patient support device of claim 17, wherein the pivotable headrest frame has at least one cutout to slidably fit over the indexing ladder.

29. A patient support device of claim 28, wherein the pivotable headrest frame further comprises a slide locking mechanism for releasably locking the pivotable headrest frame to the indexing ladder, and wherein the slide locking mechanism has at least one indexing tab and the indexing ladder has at least one slot for slidably receiving the indexing tab.

30. A patient support device or claim 29, wherein at least one movable slide post is connected to the slide locking mechanism for retracting the at least one indexing tab, and wherein the slide locking mechanism is capable of one-handed operation.

31. A patient support device of claim 2, wherein the buttock restraint means is a pad, block, or cushion.

32. A patient support device of claim 2, wherein the buttock restraint means is a adjustable protrusion and the protrusion restricts the patient's movement on the device.

* * * * *